United States Patent [19]
Larsson et al.

[11] Patent Number: 5,792,214
[45] Date of Patent: Aug. 11, 1998

[54] APPARATUS AND METHOD FOR TREATING NEONATAL HYPERBILIRUBINEMIA

[75] Inventors: Michael Larsson, Baar; Hans R. Kunzler, Mettmenstetten, both of Switzerland

[73] Assignee: Medela, Inc., McHenry, Ill.

[21] Appl. No.: 381,537

[22] Filed: Jan. 31, 1995

[51] Int. Cl.⁶ .................................................. D61N 5/00
[52] U.S. Cl. .......................... 607/88; 607/90; 362/130; 362/32; 5/498
[58] Field of Search .......................... 5/498, 600, 602, 5/923; 362/130, 32, 260, 2; 607/88–94

[56] References Cited

U.S. PATENT DOCUMENTS

| | | | |
|---|---|---|---|
| 3,822,706 | 7/1974 | Simone et al. | 600/22 |
| 3,877,437 | 4/1975 | Maitan et al. | 600/22 |
| 4,081,150 | 3/1978 | Tyson. | |
| 4,234,907 | 11/1980 | Daniel. | |
| 4,328,533 | 5/1982 | Paredes. | |
| 4,734,945 | 4/1988 | Wright | 5/603 |
| 4,736,088 | 4/1988 | Bart. | |
| 4,754,372 | 6/1988 | Harrison. | |
| 4,761,047 | 8/1988 | Mori. | |
| 4,802,066 | 1/1989 | Mori | 362/130 |
| 4,907,132 | 3/1990 | Parker | 362/32 |
| 5,014,376 | 5/1991 | Doran et al. | 5/603 |
| 5,339,223 | 8/1994 | Kremenchugsky et al. | 362/32 |
| 5,400,425 | 3/1995 | Nicholas et al. | 362/32 |
| 5,498,229 | 3/1996 | Barsky et al. | 600/22 |
| 5,566,413 | 10/1996 | Webb et al. | 600/22 |

OTHER PUBLICATIONS

Mèdiprèma, "Cradle 360" Literature.
A BOC Health Care Company, "Ohmeda Biliblanket Phototherapy System" Literature.
Fiberoptic Medical Products, Inc., "Fiberoptic Phototherapy Device" Literature.
Fiberoptic Medical Products, Inc., "the Wallaby" Literature.

*Primary Examiner*—Robert L. Nasser
*Attorney, Agent, or Firm*—Brinks Hofer Gilson & Lione

[57] ABSTRACT

An apparatus for irradiating an infant includes a frame for supporting the infant, and a source of radiation positioned below the frame and the infant. The frame includes a fully transparent section for allowing the radiation to pass therethrough to the infant.

18 Claims, 7 Drawing Sheets

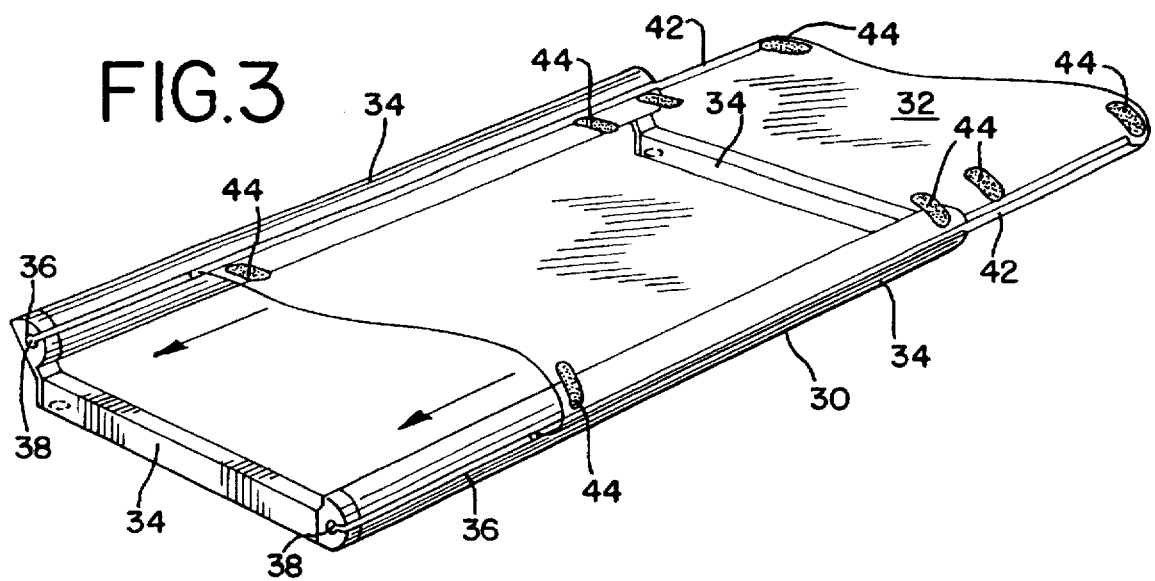
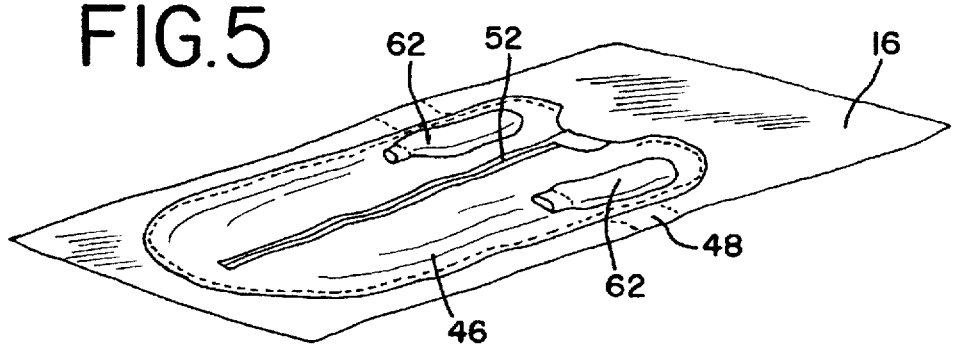
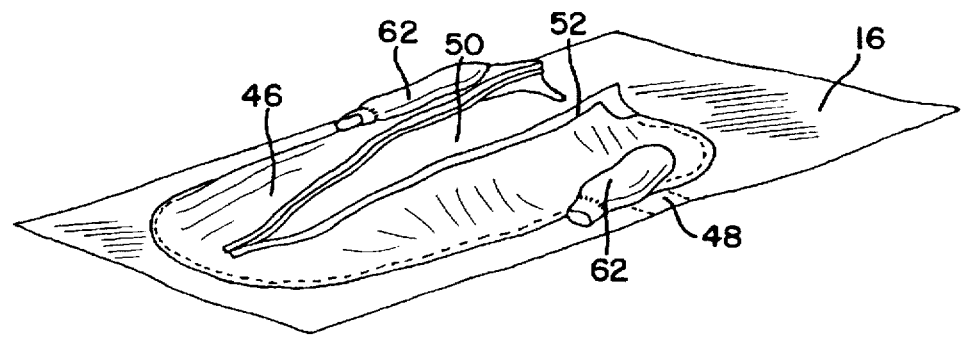

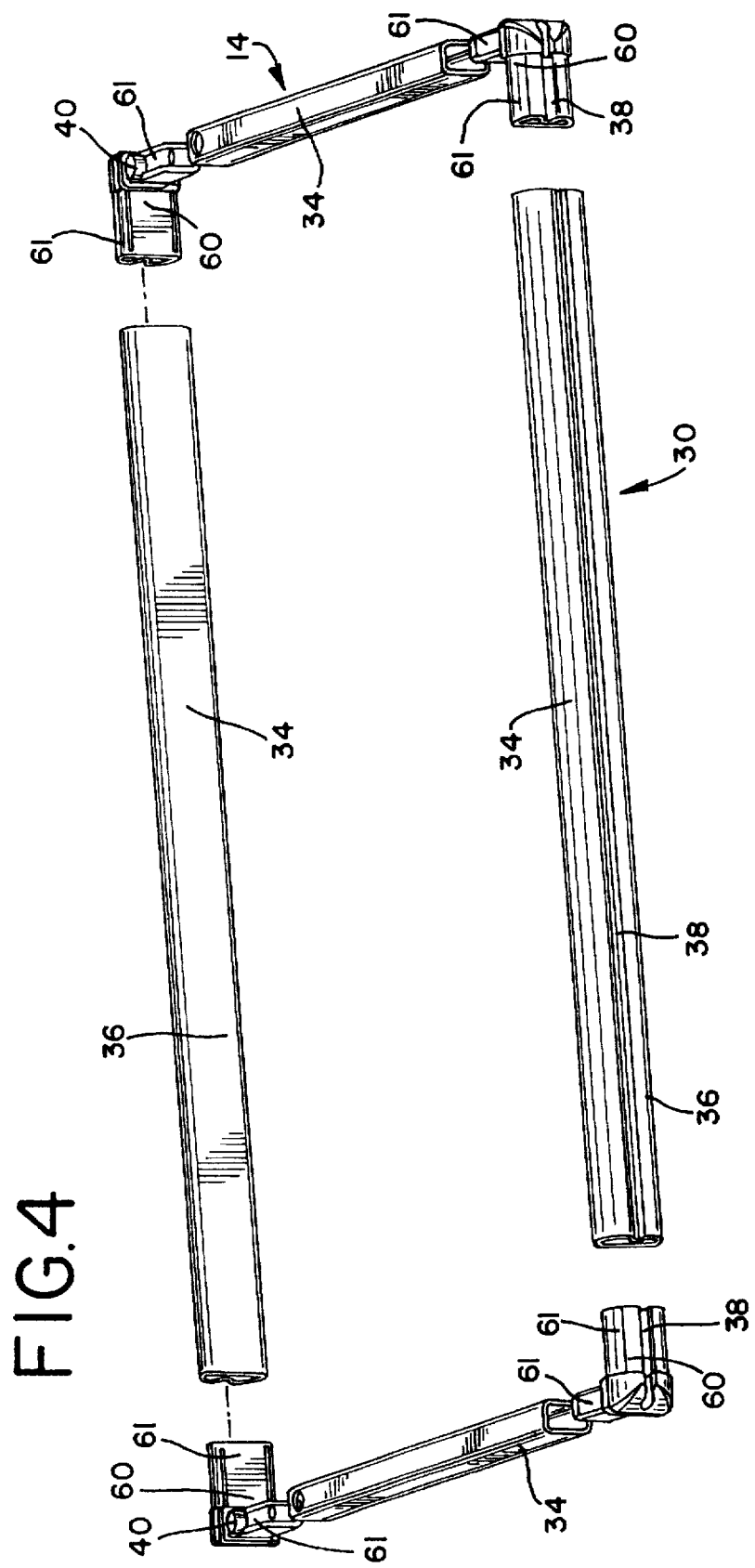

5,792,214

1

APPARATUS AND METHOD FOR TREATING NEONATAL HYPERBILIRUBINEMIA

BACKGROUND OF THE INVENTION

The present invention is directed generally to the treatment of neonatal hyperbilirubinemia and, more particularly, to an improved apparatus and method for treating neonatal hyperbilirubinemia.

Excessive levels of serum-bilirubin in newborn infants causes a condition called neonatal hyperbilirubinemia. Hyperbilirubinemia is treated by irradiating the affected infants with therapeutic levels of light within a given wavelength range (e.g., within the blue light range of the light spectrum). For best results, the blue light radiation should be evenly distributed over the entire surface of the affected infants' bodies.

One conventional treatment method requires placing blue light sources above the affected infants' hospital cribs and irradiating the infants from above. While this "overhead" phototherapy treatment has provided satisfactory results, the infants must be rolled over (from their fronts to their backs, and vice-versa) during treatment to insure even distribution of the blue light radiation. In addition, the use of overhead light sources results in less free space being available in typically cramped hospital rooms.

A second conventional treatment for hyperbilirubinemia includes a self-contained therapy apparatus for supporting and irradiating the affected infants. The apparatus includes a circular phototherapy hood having an array of blue light sources. The affected infants are placed on a sling-type support frame that is slidably received within the circular hood. The blue light sources are arrayed to provide a near-uniform distribution of radiation along practically the entire surface of the infants' bodies. While this "all around" treatment method has its advantages over the "overhead" treatment method described above in that it practically eliminates the need for rolling the infants over during treatment, the apparatus is expensive, is not adaptable for use with regular hospital cribs and, because it is a self-contained unit, is not readily portable.

In addition, because the blue light radiation should be evenly distributed over the infants' bodies for best results, conventional treatments have used active arm and/or leg restraints to keep the infants from rolling over or otherwise moving during treatment. As can be imagined, these active restraints have caused the newborn infants to become uncomfortable and restive during treatment.

SUMMARY OF THE INVENTION

The present invention provides an apparatus for treating hyperbilirubinemia that is portable and useable with regular hospital cribs or cots. In addition, the apparatus provides a passive restraint system that is designed to hold the affected infants in a relatively comfortable and unrestrictive manner during treatment. In a preferred embodiment of the present invention, the apparatus includes a transparent cot-like structure for supporting an infant above a blue light irradiation unit.

According to a first aspect of the present invention, an apparatus for irradiating an infant includes a frame for supporting the infant, and a source of radiation positioned below the frame and the infant. The frame includes a fully transparent section for allowing the radiation to pass therethrough to the infant.

According to a second aspect of the present invention, an apparatus for irradiating an infant includes an irradiation

2 unit insertable in a cot in place of a mattress, and a frame operable to support the infant above the irradiation unit. The irradiation unit includes a source of radiation and a transparent upper surface disposed above the source of radiation. In addition, the frame includes a transparent foil positioned above the irradiation unit. In a dependent aspect, the apparatus further includes a therapy blanket detachably connected to the frame to cover the infant. The therapy blanket includes a transparent section through which radiation can pass to the infant. In a preferred aspect, the therapy blanket defines a pouch having a pair of sleeves for passively restricting the infant to be treated.

According to a third aspect of the present invention, a cot for supporting an infant for phototherapy treatment is provided. The cot includes a frame having a pair of opposed side members, and a transparent sheet material connected to the pair of opposed side members. At least one of the opposed side members is hingedly attached to the frame. In a preferred aspect, each of the side members defines a groove through which the ends of the transparent sheet material are pulled to attach the sheet material to the frame.

According to a fourth aspect of the present invention, a method for treating hyperbilirubinemia is provided, which comprises the following steps: providing a source of radiation in place of a mattress of a cot; providing a frame for supporting an infant to be treated, the frame including a transparent material; placing the frame above the source of radiation; placing the infant on the transparent material of the frame; and irradiating the infant. In a preferred aspect, the infant is passively restrained within a pouch defined in a blanket detachably connected to the frame.

The present invention provides an apparatus for treating hyperbilirubinemia that saves space, is easy to use, and is less expensive than other conventional apparatuses. Moreover, because the present invention can be used with a regular hospital crib, the infant may be treated in close proximity to its mother, which makes the infant feel comfortable and aids in mother/infant bonding. In addition, the treatment apparatus provides light that is precisely directed a minimum distance to the affected infant, which results in superb therapeutic performance.

These and other features and advantages of the present invention will be further understood upon consideration of the following detailed description of the present invention, taken in conjunction with the accompanying drawings.

BRIEF DESCRIPTION OF THE DRAWINGS

FIG. 3 is a perspective view of the therapy frame shown in FIG. 1.

FIG. 4 is an exploded and inverted view of the therapy frame shown in FIGS. 1 and 3.

FIG. 5 is a perspective view of the therapy blanket shown in FIG. 1.

FIG. 6 is a perspective view of the therapy blanket shown in FIG. 5 with the pouch opened to reveal the transparent section thereof.

DETAILED DESCRIPTION OF THE PRESENTLY PREFERRED EMBODIMENT

The hyperbilirubinemia treatment apparatus of the present invention is intended to be inserted in, and thereby used with, conventional infant hospital cribs or cots. Specifically, it is contemplated that the treatment apparatus shown and described herein can be placed on a hospital crib or cot that has had its mattress removed.

Figure 1:
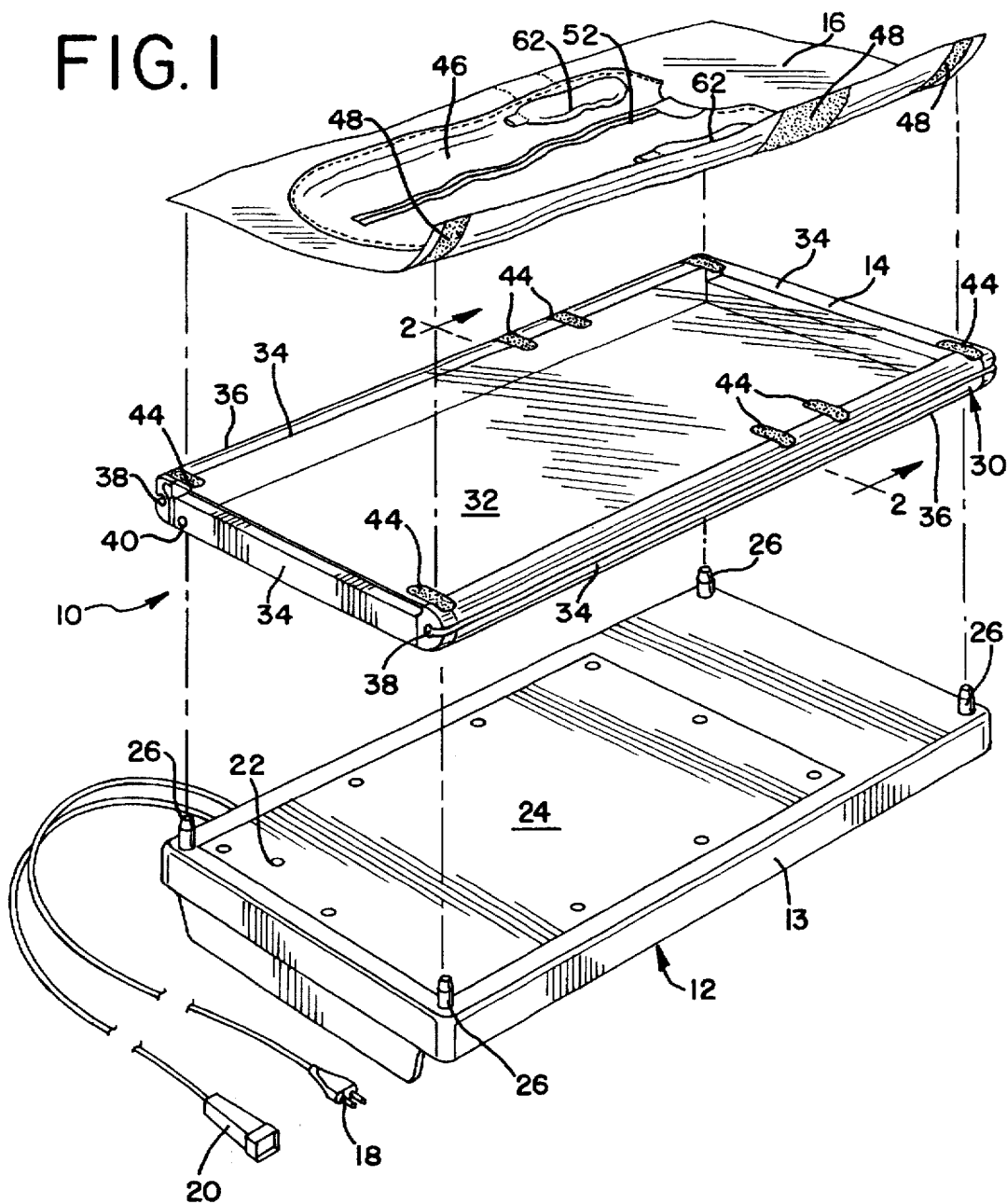
FIG. 1 is an exploded perspective view of a preferred embodiment of the hyperbilirubinemia treatment apparatus of the present invention.
Figure 2:
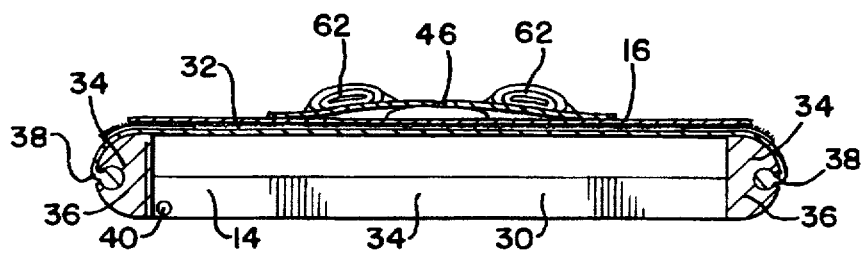
FIG. 2 is a cross-sectional view taken along line 2—2 of FIG. 1.

Turning now to the drawings, FIG. 1 shows an exploded view of the components of the preferred embodiment of the hyperbilirubinemia treatment apparatus 10 of the present invention. As shown, the apparatus 10 generally includes an irradiation unit 12, an infant support therapy frame 14, and a therapy blanket 16.

Figure 7:
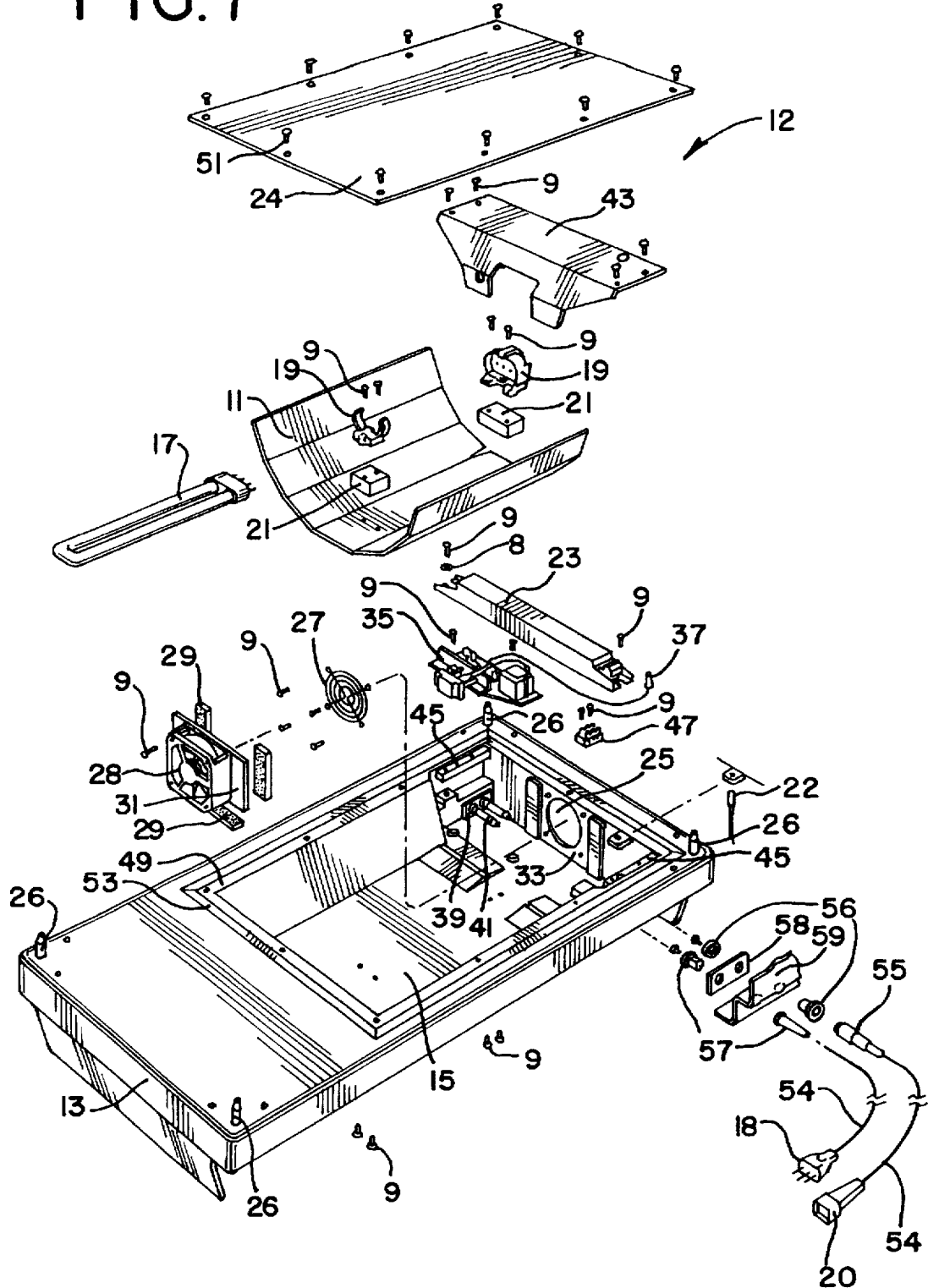
FIG. 7 is an exploded view of the irradiation unit shown in FIG. 1.

As shown in FIGS. 1 and 7, the irradiation unit 12 comprises a base 13 having a recess 15, in which are housed the major components of the irradiation unit 12. As best shown in FIG. 7, the irradiation unit 12 contains a highly-polished aluminum reflector 11, above which is supported a compact fluorescent tube 17. Preferably, the light tube 17 emits light in the 420-480 nanometer range, which has been found to be therapeutic for treating hyperbilirubinemia. The tube 17 is supported within the irradiation unit 12 by means of two lamp supports 19, which are in turn supported above the reflector 11 by two spacers 21. In addition, the tube 17 is connected to a ballast 23 mounted within the irradiation unit 12. Unless otherwise specified, the components disposed within the irradiation unit 12 are preferably mounted therein by means of conventional washers 8 and screws 9.

As further shown in FIG. 7, the recess 15 includes an aperture 25 having a fan grille 27 mounted therein. A rotary fan 28 is mounted within the recess 15 behind the fan grille 17 to cool the light tube 17. A plurality of foam strips 29 are placed between the fan plate 31 and the base wall 33 to reduce vibratory transmission to the base 13.

Additionally, a control unit 35 for controlling the irradiation unit 12 is mounted within the recess 15. A photosensor 37 for sensing the intensity of the light emitted from the tube 17, an LED display 22 and a 3-pole terminal block 47, are interfaced with the control unit 35. The function of the control unit 35, the photosensor 37, the LED display 22 and the terminal block 47, and additional components, will be described in detail below.

Furthermore, as shown in FIG. 7, a twist-fit fuse 39 (which is held in a fuseholder 41) for the irradiation unit 12 is positioned within the recess 15.

The above-mentioned components of the irradiation unit 12 are covered, at least in part, by a cover 43 mounted on brackets 45 positioned near the top edge of the recess 15. As shown in FIGS. 1 and 7, the recess 15 of the irradiation unit 12 is covered by a plate 24. Preferably, the plate 14 is transparent, water-proof and formed of Perspex or Plexiglass. The plate 24 is preferably attached to the upper edge 49 of the base 13 by a plurality of slotted screws 51. In addition, a seal 53 may be provided between the upper edge 49 of the base 13 and the plate 24. As best shown in FIG. 1, the LED display 22 is positioned in the plate 24 for viewing by hospital personnel.

As further shown in FIGS. 1 and 7, the irradiation unit 12 is provided with a power plug 18 for powering the unit 12 and a start/stop switch 20 for activating/deactivating the unit 12. The cords 54 for the plug 18 and the switch 20 are connected to the unit 12 by a cord connector 55 (which preferably includes a fuse, such as a twist-fit fuse) and a cord bushing 56, and a cable clamp 57, respectively. A support bracket 58 may be placed behind the outer wall 59 of the base 13 to support the mounting elements 55, 56, 57 for the plug 18 and the switch 20.

Further, the irradiation unit 12 is provided with a plurality of support posts 26, which are used to support the infant support therapy frame 14 above the irradiation unit 12.

As shown in FIGS. 1-4, the therapy frame 14 preferably includes an aluminum frame 30 and a transparent plastic foil material 32 for supporting the infant above the irradiation unit 12. As will be described below, the foil 32 includes a plurality of connectors 44, which are preferably Velcro fasteners. As shown, the frame 30 is preferably rectangular in shape and generally includes four hollow frame members 34. As best shown in FIG. 4, the frame members 34 are preferably interconnected by four corner units 60. Each of the corner units 60 has ends 61 that are insertable into the hollow frame members 34. Two of the opposed frame members 36 are rounded and include longitudinal grooves 38 therein. At least one of the frame members 36 is hingedly attached to the frame 30.

To attach the foil 32 to the frame 30, at least one of the frame members 36 is unhinged and opened via the buttons 40, as best shown in FIG. 3. The ends 42 of the foil 32 are inserted within the grooves 38 until the length of the foil 32 is fully emplaced. At that point, the "open" frame member 36 is closed and the foil 32 is thereby pulled taut over the frame 30. As best shown in FIG. 1, the therapy frame 14 is then placed on and supported above the irradiation unit 12 by means of the support posts 26.

Next, the therapy blanket 16 is placed on the therapy frame 14. As shown in FIGS. 1, 5 and 6, the therapy blanket 16 includes a pouch 46 for holding the infant to be treated and, on the underneath of the blanket 16, a number of connectors 48, which are preferably Velcro fasteners. The connectors 48 on the blanket 16 are connected to the connectors 44 on the therapy frame 14 to properly position and hold the blanket 16 in place thereon.

As best shown in FIGS. 5 and 6, the pouch 46 includes a pair of sleeves 62 for receiving and holding the arms of the infant. In addition, a zipper 52 or other suitable closure device is used to open and close the pouch 46.

As best shown in FIG. 6, the blanket 16 includes a transparent section 50 under the pouch 46. The transparent section 50 is required to allow the light from the irradiation unit 12 to be transmitted through the blanket 16 to the infant.

To insure optimum therapeutic effect, the infant must be placed within the pouch 46 on the transparent section 50. The pouch 46 passively restrains the infant from moving outside of the irradiation area of the light tube 17. As can be seen, the pouch 46 renders arm and leg restraints unnecessary for the treated infant. Because the pouch 46 is soft and roomy, the infant is comfortable therein and does not feel "cramped." Consequently, the treated infant does not become restive during treatment. In addition, to provide "even" phototherapy treatment, the infant should be repositioned (i.e., switched from laying on its back to its front) periodically. Further, for best treatment results, the infant should wear diapers that are as little as possible.

Figure 8:
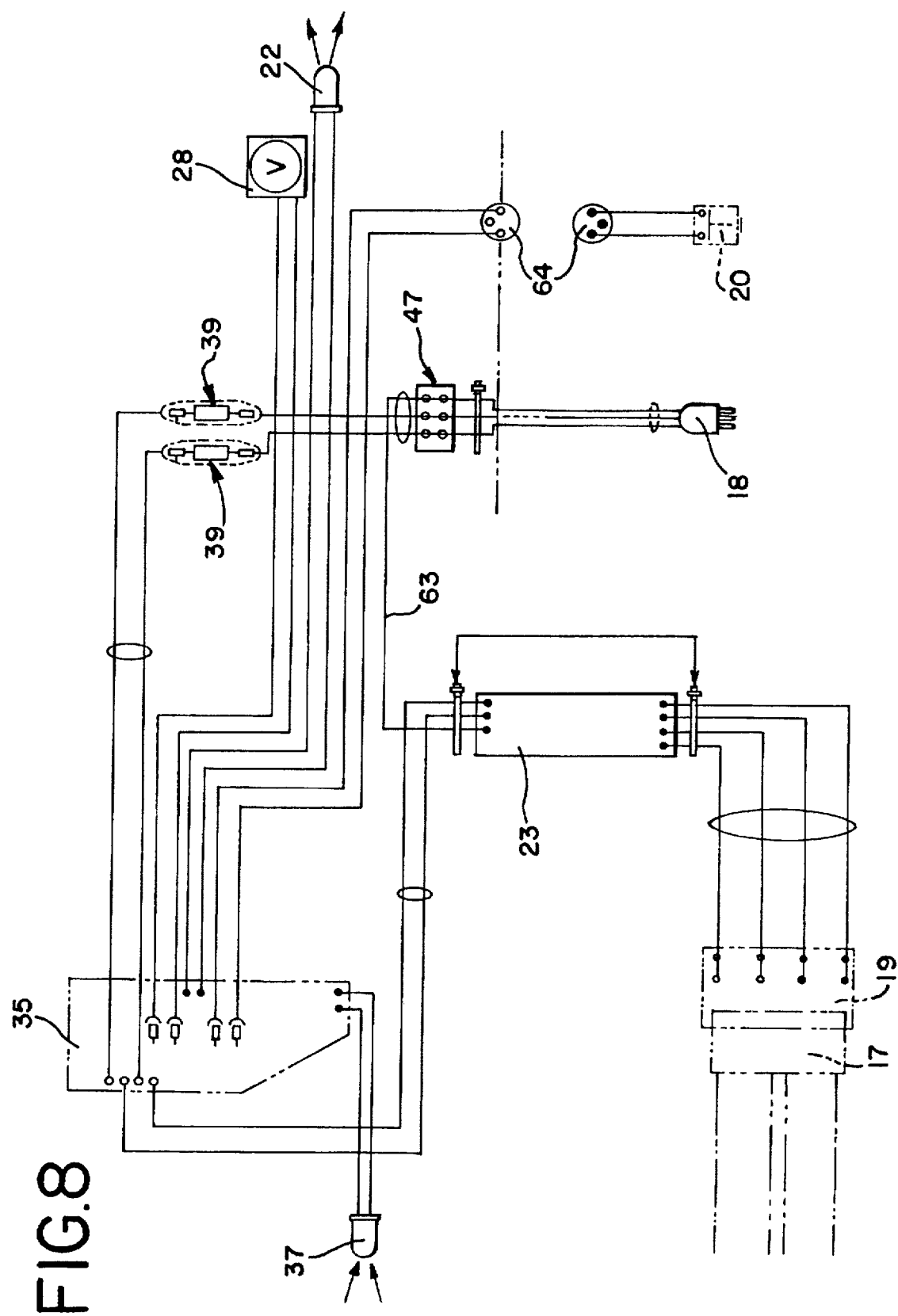
FIG. 8 is a schematic diagram of the irradiation unit shown in FIGS. 1 and 7.

A schematic diagram for the irradiation unit 12 is depicted in FIG. 8. As shown, the power plug 18 (which is preferably connected to a 230 V power source), the LED display 22, the fan 28, the photosensor 37, the light tube 17 and the optional start/stop switch 20 are interfaced with the control unit 35, the internal components of which are described below.

The power plug 18 is connected to the control unit 35 through the terminal block 47 and the set of fuses 39. The light tube 17 is connected to the lamp support 19, which is in turn connected to the electronic ballast 23. The ballast 23 is interfaced directly with the control unit 35. As shown in FIG. 8, a ground wire 63 runs from the power plug 18 through the terminal block 47 and is connected to the ballast 23.

If the operator of the treatment apparatus 10 does not desire that the irradiation unit 12 (and thus the light tube 17) be continuously activated when the power plug 18 is inserted into a power source, the optional start/stop switch 20 can be connected to the control unit 35. To alleviate the logistical and wiring problems caused by making separate control units for "switch" or "non-switch" treatment apparatuses, the control units are all preferably wired for the switch 20. If an operator desires an apparatus 10 having a start/stop switch 20 (either at purchase or subsequent to purchase), the switch 20 can be easily plugged into the control unit 35 by means of mating connectors 64, as shown in FIG. 8.

As described above, the irradiation unit 12 contains a photosensor 37 that measures the intensity of the light emitted by the light tube 17. The control unit 35 contains a comparator, such as an operational amplifier, that compares the light intensity measured by the photosensor 37 with a pre-determined, therapeutic light intensity level. If the proportion of the light emitted by the light tube 17 falls below the pre-determined-intensity level (approximately 70% of optimum irradiation flow), the comparator causes the control unit 35 to activate the LED display 22. The activated LED display informs the hospital or other personnel that the light tube 17 needs to be changed.

As previously mentioned, to insure that the hyperbilirubinemia treatment apparatus 10 operates correctly, sufficient air must be circulated around the light tube 17. To that end, a fan 28 is included in the irradiation unit 12 to cool the light tube 17, and to prevent the infant from becoming overheated. In addition, to maintain the flow of air and the temperature balance of the apparatus 10, the hospital cot in which the apparatus 10 is placed should have ventilation openings having a combined minimum area of 20 cm².

Figure 9:
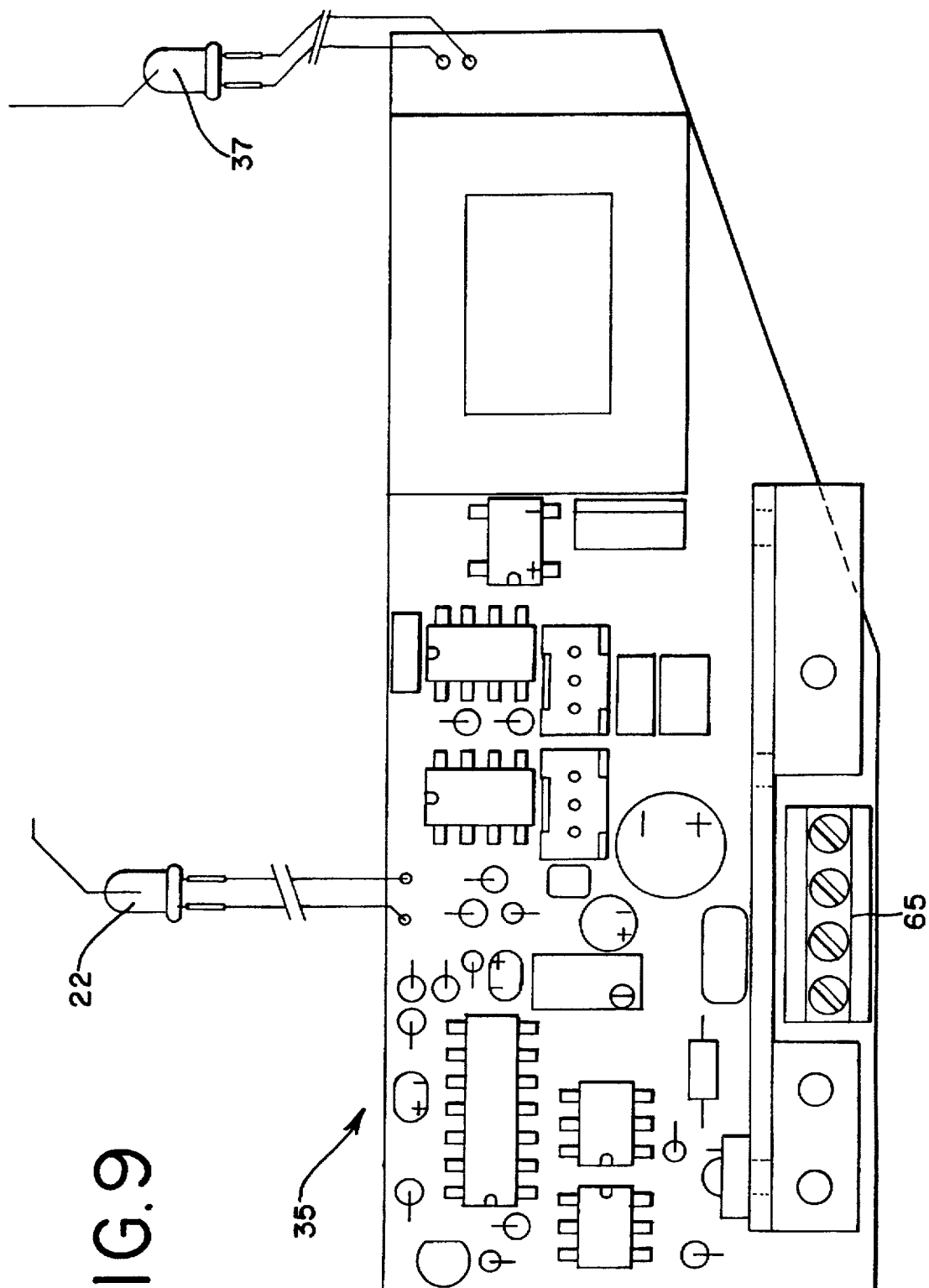
FIG. 9 is a schematic diagram of the control unit shown in FIG. 8.

FIG. 9 shows the internal components of the control unit 35. As shown, the photosensor 37 and the LED display 22 are connected to the control unit 35. The control unit contains four connector leads 65 for wiring the power plug 18 and the light tube 17 thereto. In addition, as shown by the data catalog numbers listed thereon, the control unit 35 includes a variety of conventional electronic components, including resistors, capacitors, integrated circuits and transistors. The part names, schematics and manufacturers of the components shown in FIG. 9 may be found in any conventional Semiconductor Databook, which information is hereby incorporated by reference.

Figure 10:
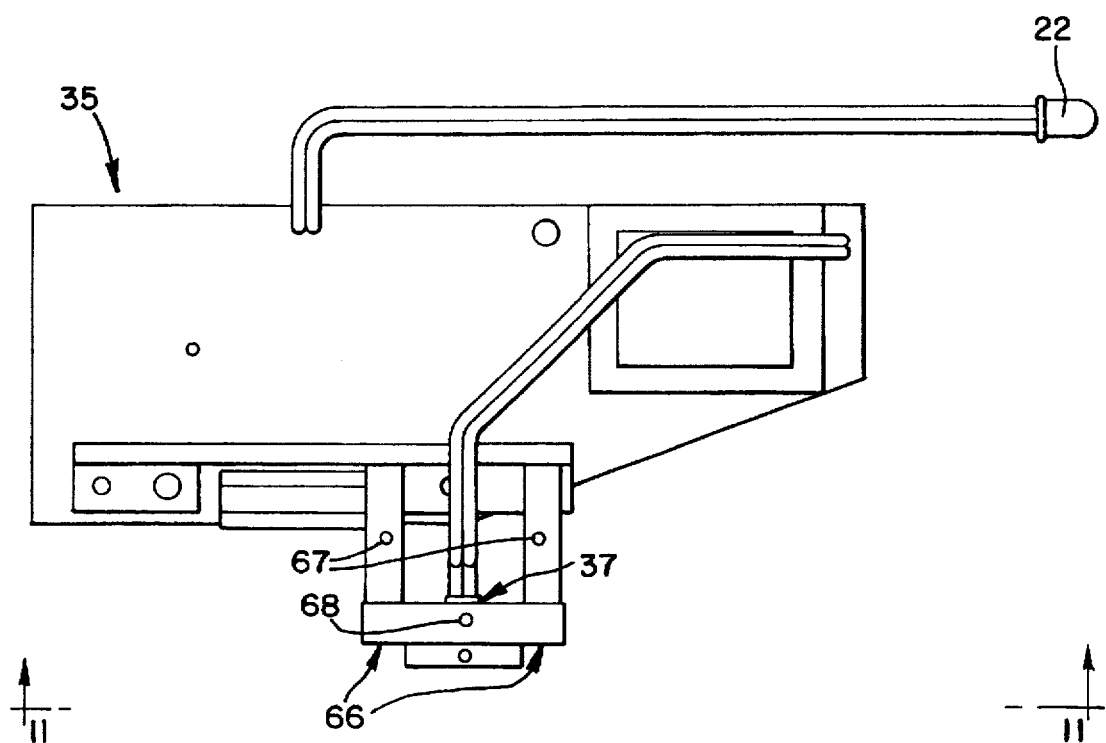
FIG. 10 is a plan view of the control unit shown in FIGS. 7, 8 and 9.
Figure 11:
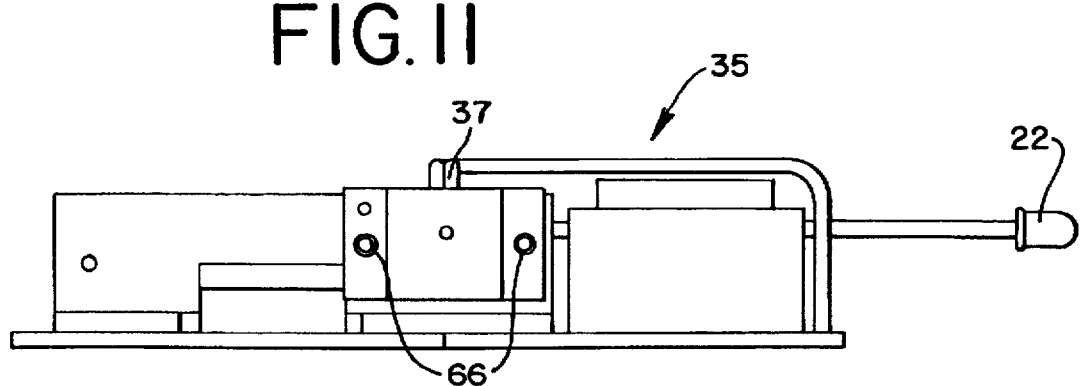
FIG. 11 is a side view taken along line 11—11 of FIG. 10.

FIGS. 10 and 11 show plan and side views, respectively, of the control unit 35 shown in FIGS. 7–9. As shown, the LED display 22 and the photosensor 37 are wired into the control unit 35. In addition, the photosensor 37 is mounted on a support bracket 68, which in turn is mounted on the control unit 35 by support posts 67. Mounting members 66, which preferably comprise screws, are inserted through the bracket 68 and the posts 67 to secure the photosensor 37 to the control unit 35.

The preferred materials and specifications of the hyperbilirubinemia treatment apparatus 10 of the present invention are presented below. The irradiation unit 12 preferably requires a power supply of 230 Volts ±10% (operating at 50 Hz), consumes approximately 20 Watts of power during use, has dimensions of L68 cm×W35.4 cm×H4.2 cm and a mass of 3.8 Kg. The light tube 17 is an Osram Dulux-L, color-code 71, 18 Watt compact fluorescent tube, which has been developed especially for phototherapy. The light tube 17 has an approximate useful life of 1,500 hours. In addition, the fuses 39 used in the irradiation unit 12 are preferably Type 05×20, 250 V/T 315 mA.

The infant support therapy frame 14 preferably has dimensions of L68 cm×W35.4 cm×H4.2 cm and a mass of 1.2 Kg. Further, the foil 32 preferably is formed of skin-friendly polyurethane (PUR).

The present invention provides an apparatus 10 for treating hyperbilirubinemia that passively restrains an infant on a transparent support surface, and irradiates the infant from below with therapeutic levels of light. In a preferred embodiment, the apparatus 10 can be placed in a regular hospital crib in place of the mattress. This allows the infant to be treated in the same room as the mother, which makes the infant feel comfortable and facilitates mother/child bonding, and saves on limited hospital space. In addition, the use of the apparatus 10 in regular hospital cribs allows incubators and other equipment to be used for infants with other pressing medical conditions, thereby freeing up expensive medical equipment.

It should be appreciated that the phototherapy treatment apparatus 10 of the present invention may be modified or configured as appropriate for the application. The embodiment described above is to be considered in all respects only as illustrative and not restrictive. Changes may be made without departing from the spirit of the invention. The scope of the invention is indicated by the following claims rather than by the foregoing description. All changes which come within the literal meaning as well as the range of equivalency of the claims are to be embraced within their scope.

What is claimed is:

1. An apparatus for irradiating an infant comprising:
   a frame having a transparent section adapted to support an infant thereon, the transparent section operable to allow radiation to pass therethrough;
   a source of radiation positioned below the frame; and
   a therapy garment connected to the frame, said therapy garment defining portions within which limbs of the infant are received for holding the infant in Position over the source of radiation.

2. The apparatus of claim 1 wherein the therapy blanket is detachably connected to the frame by mating connectors.

3. The apparatus of claim 1 wherein the therapy garment has an upper and a lower layer which define a pouch within which the infant is received for holding the infant in position over the source of radiation, said garment having an opening in said lower layer overlying said transparent section through which radiation from said source can pass.

4. An apparatus for irradiating an infant comprising:
   a frame having a transparent section adapted to support an infant therein, the transparent section operable to allow radiation to pass therethrough;
   a source of radiation positioned below the frame and the infant;
   a therapy blanket detachably connected to the frame and defining a pouch for holding the infant in position over the source of radiation, with a pair of sleeves for receiving the arms of the infant.

5. The apparatus of claim 4 wherein the therapy blanket further comprises a radiation transparent area of the pouch overlying the transparent section of the frame.

6. An apparatus for irradiating an infant comprising:

an irradiation unit insertable in a bed in place of a mattress, the irradiation unit comprising a source of radiation for treating the infant;

a frame operable to support the infant above and spaced from the irradiation unit, the frame comprising a framework and a radiation-transparent material which is held taut within the frame members, the radiation-transparent material forming a support surface upon which the infant is suspended above and spaced from the irradiation unit; and a therapy blanket detachably connected to the frame and adapted to cover the infant, the therapy blanket having an area through which radiation from the source of radiation can pass to the infant.

7. The apparatus of claim 6 wherein the therapy blanket further comprises a pouch for holding the infant above the transparent section.

8. The apparatus of claim 7 wherein the pouch defines a pair of sleeves for receiving the arms of the infant.

9. The apparatus of claim 6 wherein the source of radiation comprises a blue light fluorescent tube.

10. An apparatus for radiation treatment of a patient, comprising:

a source of radiation for treating the patient;

a frame having spaced apart side frame members;

a material transparent to said radiation, said material being held taut within and between said frame members and forming a resilient cot-like support surface for supporting the patient thereon;

means for locating said frame and material transparent to said radiation above and spaced from said source of radiation; and a restraining garment attached to said frame, said restraining garment having a portion within which a pair of the patient's limbs are receivable to locate and hold the patient in a desired position said restraining garment further including an area through which radiation can pass overlying said material transparent to said radiation.

11. An apparatus for phototherapy treatment of a patient, comprising:

a source of phototherapeutic radiation enclosed in a base which is insertable into a bed in place of a mattress for treating the patient; and a bed having a frame with substantially rigid side frame members and a resilient support surface inserted into and held taut within said frame members, said support surface including material transparent to said radiation, said frame members being carried on said base and positioning said support surface above and closely spaced to said source of radiation.

12. An apparatus for radiation treatment of a patient, comprising:

a source of radiation for treating the patient;

a support surface upon which the patient is received;

a framework upon which said support surface is carried for exposure to said radiation;

a material transparent to said radiation, said material transparent to said radiation forming at least part of said support surface; and a restraining garment mounted to said support surface adapted to receive the patient therein, said garment having a section through which radiation can pass with at least a portion of said garment section overlying said material transparent to said radiation.

13. An apparatus for radiation treatment of a child, comprising:

a source of radiation for treating the child wherein said source of radiation is a phototherapy light source;

a support surface upon which the child is received;

a framework upon which said support surface is carried, said framework positioning said support surface spaced from said source of radiation in a location to be exposed to said radiation:

a material transparent to said radiation, said material transparent to said radiation forming at least part of said support surface, said material transparent to said radiation being substantially transparent to light from said phototherapy light source; and a restraining garment mounted to said support surface adapted to receive the child therein, with at least a portion of said garment having an opening formed therein overlying said material transparent to said radiation, said restraining garment having arms adapted to receive a child's arms therein.

14. An apparatus for radiation treatment of a child, comprising:

a source of radiation for treating the child wherein said source of radiation is a phototherapy light source, a support surface upon which the child is received:

a framework upon which said support surface is carried, said framework positioning said support surface spaced from said source of radiation in a location to be exposed to said radiation;

a material transparent to said radiation, said material transparent to said radiation forming at least part of said support surface, said material transparent to said radiation being a plastic sheet material substantially transparent to light from said phototherapy light source; and a restraining garment mounted to said support surface adapted to receive the child therein, with at least a portion of said garment having an opening formed therein overlying said material transparent to said radiation, said restraining garment being adapted to receive the child therein and including sleeves adapted to receive a child's arms therein, said restraining garment having a portion which provides an opening to light from said phototherapy light source, said restraining garment being removably attached to said support surface to position the child with said opening overlying said plastic sheet material.

15. An apparatus for radiation treatment of a child, comprising:

a source of radiation for treating the child;

a support surface upon which the child is received;

a framework upon which said support surface is carried, said framework positioning said support surface spaced from said source of radiation in a location to be exposed to said radiation;

a material transparent to said radiation said material transparent to said radiation forming at least part of said support surface, and a restraining garment mounted to said support surface adapted to receive the child therein, with at least a portion of said garment having an opening formed therein overlying said material transparent to said radiation;

said restraining garment comprising a blanket having sleeves formed therein within which a child's arms are received.

16. The apparatus of claim 15 wherein said restraining garment is removably attached to said support surface, and further includes an opening in said blanket through which said child can be inserted and removed from said blanket when said blanket is attached to said support surface.

17. An apparatus for phototherapy treatment of a patient, comprising:

a source of phototherapy light for treating the patient;

a flexible support surface upon which the patient is received;

a framework within which said support surface is held to suspend the patient above and spaced from said source of phototherapy light for exposure to said radiation; and a material transparent to said radiation, said material transparent to said radiation forming at least part of said support surface; and a restraining garment mounted to said support surface adapted to receive the patient therein, with at least a portion of said garment providing an opening to said garment overlying said material transparent to said radiation when said garment is mounted to said support surface.

18. An apparatus for radiation treatment of a child, comprising:

a source of radiation for treating the child comprising a fluorescent light source of a desired wavelength, said light source being enclosed in a base which is sized to fit into an incubator;

a support surface upon which the child is received;

a framework upon which said support surface is carried, said framework positioning said support surface above and closely spaced from said source of radiation in a location to be exposed to said radiation;

a material transparent to said radiation, said material transparent to said radiation forming at least part of said support surface; and a restraining garment mounted to said support surface adapted to receive the child therein, with at least a portion of said garment having an opening formed therein overlying said material transparent to said radiation.

* * * * *